United States Patent
Zou et al.

(10) Patent No.: US 8,542,895 B2
(45) Date of Patent: Sep. 24, 2013

(54) METHODS AND SYSTEMS FOR COLOR FLOW DYNAMIC FRAME PERSISTENCE

(75) Inventors: Yaoxian Zou, Shenzhen (CN); Bin Yao, Shenzhen (CN); Qinjun Hu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 290 days.

(21) Appl. No.: 12/960,190

(22) Filed: Dec. 3, 2010

(65) Prior Publication Data

US 2011/0164794 A1 Jul. 7, 2011

(30) Foreign Application Priority Data

Jan. 5, 2010 (CN) .......................... 2010 1 0042708

(51) Int. Cl.
*G06K 9/00* (2006.01)
(52) U.S. Cl.
USPC ........... 382/128; 382/129; 382/130; 382/131; 600/454; 600/504
(58) Field of Classification Search
USPC .......................... 382/128–131; 600/454, 504
See application file for complete search history.

(56) References Cited

U.S. PATENT DOCUMENTS

| | | | | |
|---|---|---|---|---|
| 5,555,886 A * | 9/1996 | Weng et al. | ...... | 600/454 |
| 5,699,446 A * | 12/1997 | Rougee et al. | ...... | 382/130 |
| 5,768,405 A * | 6/1998 | Makram-Ebeid | ...... | 382/128 |
| 5,991,697 A * | 11/1999 | Nelson et al. | ...... | 702/49 |
| 6,263,089 B1 * | 7/2001 | Otsuka et al. | ...... | 382/107 |
| 6,430,315 B1 * | 8/2002 | Makram-Ebeid | ...... | 382/197 |
| 6,464,641 B1 * | 10/2002 | Pan et al. | ...... | 600/453 |
| 6,728,561 B2 * | 4/2004 | Smith et al. | ...... | 600/323 |
| 7,066,888 B2 * | 6/2006 | Abend et al. | ...... | 600/454 |
| 7,486,811 B2 * | 2/2009 | Kaufman et al. | ...... | 382/128 |
| 7,505,549 B2 * | 3/2009 | Ohishi et al. | ...... | 378/4 |
| 7,536,043 B2 * | 5/2009 | Fan et al. | ...... | 382/128 |
| 7,727,153 B2 * | 6/2010 | Fritz et al. | ...... | 600/449 |
| 7,738,626 B2 * | 6/2010 | Weese et al. | ...... | 378/41 |
| 7,738,685 B2 * | 6/2010 | Hyun et al. | ...... | 382/128 |
| 7,758,507 B2 * | 7/2010 | Yoshikawa et al. | ...... | 600/441 |
| 7,869,306 B2 * | 1/2011 | Bick | ...... | 367/118 |
| 7,929,744 B2 * | 4/2011 | Dong | ...... | 382/128 |
| 8,047,989 B2 * | 11/2011 | Oshiki et al. | ...... | 600/437 |
| 8,057,760 B2 * | 11/2011 | Tajima | ...... | 422/547 |
| 8,121,375 B2 * | 2/2012 | Hu | ...... | 382/131 |
| 8,126,232 B2 * | 2/2012 | Dikici et al. | ...... | 382/128 |

(Continued)

FOREIGN PATENT DOCUMENTS

| CN | 1725981 A | 1/2006 |
|---|---|---|
| CN | 101431942 A | 5/2009 |

(Continued)

OTHER PUBLICATIONS

Aylward, Initialization, noise, singularities, and Scale, Feb. 2002, IEEE Medical Imaging.*

(Continued)

*Primary Examiner* — Jayesh A Patel
*Assistant Examiner* — Iman K Kholdebarin
(74) *Attorney, Agent, or Firm* — Kory D. Christensen; Stoel Rives LLP

(57) ABSTRACT

Methods and systems for color flow dynamic frame persistence in ultrasonic imaging are provided.

8 Claims, 5 Drawing Sheets

(56) References Cited

U.S. PATENT DOCUMENTS

| | | | | |
|---|---|---|---|---|
| 8,301,224 B2* | 10/2012 | Kiraly | .......................... | 600/410 |
| 2006/0025688 A1* | 2/2006 | Hayase et al. | ................. | 600/454 |
| 2007/0149877 A1* | 6/2007 | Oshiki et al. | ................. | 600/427 |
| 2007/0161900 A1* | 7/2007 | Hagiwara | ..................... | 600/454 |
| 2008/0226189 A1* | 9/2008 | Connell | ........................ | 382/255 |
| 2008/0275351 A1* | 11/2008 | Kirchberg et al. | ............ | 600/500 |
| 2008/0298651 A1* | 12/2008 | Dong | .......................... | 382/128 |
| 2009/0005691 A1* | 1/2009 | Huang et al. | .................. | 600/476 |
| 2009/0024033 A1* | 1/2009 | Murashita | .................... | 600/443 |
| 2009/0105593 A1* | 4/2009 | Xiong et al. | ................... | 600/454 |
| 2010/0014739 A1* | 1/2010 | Kiraly | .......................... | 382/131 |
| 2010/0172554 A1* | 7/2010 | Kassab et al. | ................ | 382/128 |
| 2011/0150309 A1* | 6/2011 | Barfett et al. | ................ | 382/131 |
| 2011/0164794 A1* | 7/2011 | Zou et al. | ..................... | 382/128 |
| 2011/0196237 A1* | 8/2011 | Pelissier et al. | .............. | 600/454 |
| 2011/0235878 A1* | 9/2011 | Nakayama | ................... | 382/128 |
| 2012/0014573 A1* | 1/2012 | Lautenschlager et al. | .... | 382/128 |
| 2012/0076387 A1* | 3/2012 | Hu | ................................ | 382/131 |
| 2012/0089020 A1* | 4/2012 | Nitta et al. | .................... | 600/438 |
| 2012/0089027 A1* | 4/2012 | Andreuccetti et al. | ........ | 600/443 |
| 2012/0095332 A1* | 4/2012 | Nitta et al. | .................... | 600/437 |
| 2012/0177262 A1* | 7/2012 | Bhuiyan | ....................... | 382/128 |
| 2012/0218516 A1* | 8/2012 | Imamura | ...................... | 351/206 |

FOREIGN PATENT DOCUMENTS

| | | |
|---|---|---|
| CN | 101505664 A | 8/2009 |
| CN | 101647716 A | 2/2010 |
| WO | 0162155 A1 | 8/2001 |
| WO | WO 2004054448 A1 * | 7/2004 |

OTHER PUBLICATIONS

Bullitt et al. Symbolic description of intracerebral vessels segmented, 2001, Medical Image Analysis.*

Nordsletten, Structural morphology of renal vasculature, 2006, Am. J. Physiol/Heart.*

* cited by examiner

METHODS AND SYSTEMS FOR COLOR FLOW DYNAMIC FRAME PERSISTENCE

CROSS-REFERENCE TO RELATED APPLICATIONS

This application claims the benefit of Chinese Patent Application No. 201010042708.5, filed on Jan. 5, 2010, which is incorporated herein by reference in its entirety.

TECHNICAL FIELD

This application relates to ultrasonic imaging technology.

SUMMARY OF THE INVENTION

Disclosed herein are embodiments of methods and systems for color flow dynamic frame persistence in ultrasonic imaging.

DETAILED DESCRIPTION

Figure 1:
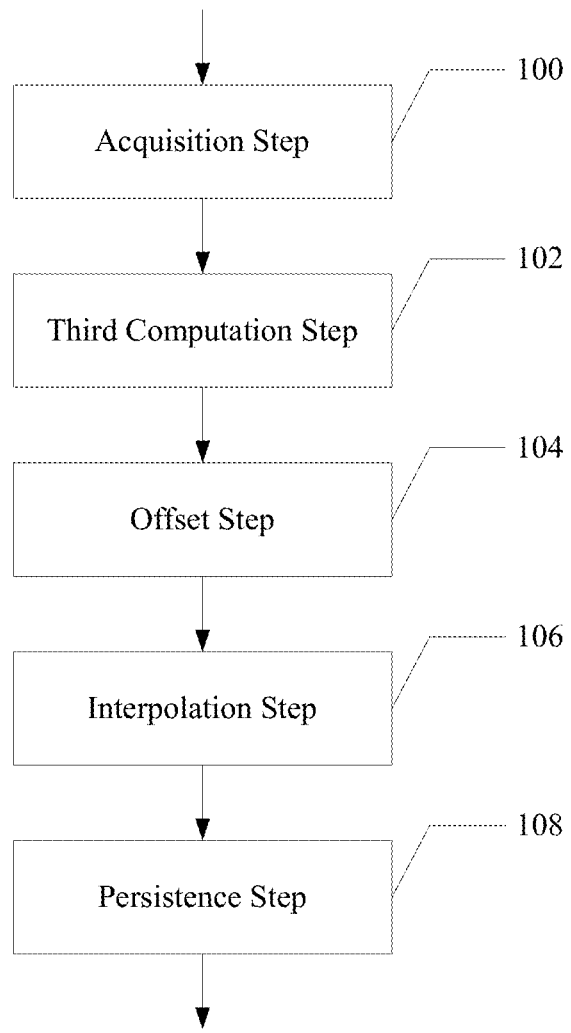
FIG. 1 is a flowchart of a method for color flow dynamic frame persistence.

Ultrasonic instruments, which are generally used in observing the tissue and structure of human body, have become crucial in medical diagnosis owing to their security, convenience, non-destruction (of tissue), and low cost. Color flow imaging technology uses the Doppler Effect to detect the existence of blood flow in human body and estimate the kinetic parameters of the flow.

In the process of color frame persistence, the SNR (Signal to Noise Ratio) of signal detection can be raised with the amount of time, such that the sensitivity for detecting faint flow signals can be improved. Typically, the operation of frame persistence is generally taken at the same position of previous and current frames, without considering the fluidity factor of flow. As there is a certain time interval Δt between the current frame and the previous frame, when calculating the flow at the current frame (i, j), the flow at the previous frame has already moved forward a certain distance along the blood vessel. If frame persistence is applied to the same position of flow between the current frame and the previous frame, the important fact that blood is flowing is ignored, and the fluidity of blood flow cannot be reflected.

According to one aspect of the disclosure, a method for calculating blood vessel direction of a flow velocity image includes distinguishing each of the points in the flow velocity image as points in a flow region and points in a background region. The method also includes estimating a rough direction of a computing point by setting a plurality of directions and respectively calculating the number of points in the flow region connecting with the computing point in each direction, and taking the direction with the maximum number of points as the rough direction of the computing point. The method further includes determining midpoints on the direction vertical to the rough direction in a neighborhood, and taking a line connecting the midpoints as a median line of the blood vessel in the neighborhood, wherein the neighborhood is centered on the computing point and includes a plurality of points in the flow region on the rough direction. The method also includes calculating the direction of the blood vessel on the computing point according to the determined median line of the blood vessel.

According to another aspect, a system for calculating blood vessel direction of a flow velocity image includes a distinguishing module configured to distinguish each of the points in the blood flow velocity image as points in a flow region and points in a background region. The system also includes an estimation module configured to set a plurality of directions and respectively calculate the number of the points in the flow region connecting with the computing point in each direction, and take the direction with the maximum number as the rough direction of the computing point. The system further includes a determination module configured to determine midpoints on the direction vertical to the rough direction in a neighborhood, and take the line connecting the midpoints as the median line of the blood vessel in the neighborhood, wherein the neighborhood takes the computing point as center and comprises a plurality of points in the flow region on the rough direction. The system also includes a computation module configured to calculate the direction of the blood vessel on the computing point according to the determined median line of the blood vessel.

According to still another aspect, a system for calculating blood vessel direction of a flow velocity image includes a distinguishing module configured to distinguish each of the points in the flow velocity image as points in a flow region and points in a background region. The system also includes an extraction module configured to extract a skeleton of the flow region from the distinguished image. The system further includes a computation module configured to calculate the direction of each point of the skeleton according to a plurality of neighbor points of each computing point of the skeleton.

According to yet another aspect, a system for color flow dynamic frame persistence includes an acquisition module configured to acquire a result of a previous frame persistence and current flow velocity image. The system also includes a computation module configured to calculate a blood vessel direction reflected by the result of the previous frame persistence. The system further includes an offset module configured to offset the result of previous frame persistence along the direction of a blood vessel with flow direction and flow velocity. The system also includes a persistence module configured to implement frame persistence between the current flow velocity image and the offset result of the previous frame persistence.

Referring to FIG. 1, a method for color flow dynamic frame persistence may include an acquisition step 100, a third computation step 102, an offset step 104, and a persistence step 108. The method may also include an interpolation step 106.

According to one embodiment, the method for color flow dynamic frame persistence comprises: acquiring the result $F_{i-1}$ of the previous frame persistence and the current flow velocity image $I_i$ (step 100); calculating the direction of the blood vessel reflected by $F_{i-1}$, which includes calculating the blood vessel direction of each point in the flow region (step 102); making an offset for $F_{i-1}$ by using the blood vessel direction, the flow direction and the flow velocity (step 104); after the offset is done, carrying out the frame persistence $\phi(I_i, F_{i-1})$ for $F_{i-1}$ and $I_i$; thus obtaining the result $F_i$ of the ith frame persistence.

The blood vessel direction is not about the positive or negative flow velocity; instead, it is about the flowing path of the blood flows in the blood vessel, and the blood flows along the flowing path. The blood vessel direction identifies the shape structure of the blood vessel. Generally, the blood vessel direction is considered approximately parallel to the blood vessel wall. When calculating the blood vessel direction, the direction of each point in the flow region needs to be calculated. The blood vessel direction can be determined by utilizing image processing methods with the spatial structure of blood vessel.

Figure 2:
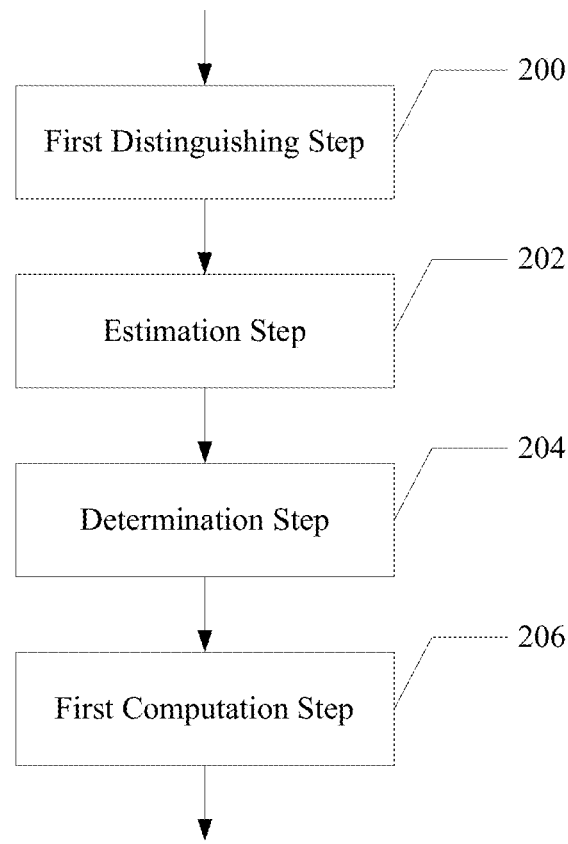
FIG. 2 is a flowchart of a method for calculating the blood vessel direction of the flow velocity image.

In one embodiment, the blood vessel direction can be calculated by using a first distinguishing step 200, an estimation step 202, a determination step 204, and a first computation step 206, as illustrated in FIG. 2. This may be accomplished by first, estimating the rough direction of the calculating point located in the blood vessel, then narrowing the calculation range, and accurately calculating the blood vessel direction in a small range. An example of the process is described below.

1. The image distinguishing (step 200) is used to distinguish which part of the image is the flow region or the background region. For example, by binarizing the input result $F_{i-1}$ of the previous frame persistence, each point in the flow velocity image can be distinguished as point in the flow region or point in the background region. The binarization can be done with a threshold, that is, marking the points whose absolute value are smaller than a threshold as zero and the remaining points as 1. Additionally, the points in the image ($F_{i-1}$) can be directly distinguished as points in the flow region and points in the background region with a predefined threshold.

2. Rough estimation of blood vessel direction may then be performed. The estimation can be done by setting the number of directions in rough estimation according to requirement for the accuracy of the system. Two directions including the vertical and horizontal directions can be set; or four directions including the directions of 0°, 45°, 90° and 135° can be set. If necessary, even eight directions can be set. One embodiment includes setting two directions, respectively calculating the number of the points consequently connected with the computing point in each direction, and taking the direction with the maximum number as the rough direction of the computing point in the flow region (step 202).

Figure 3:
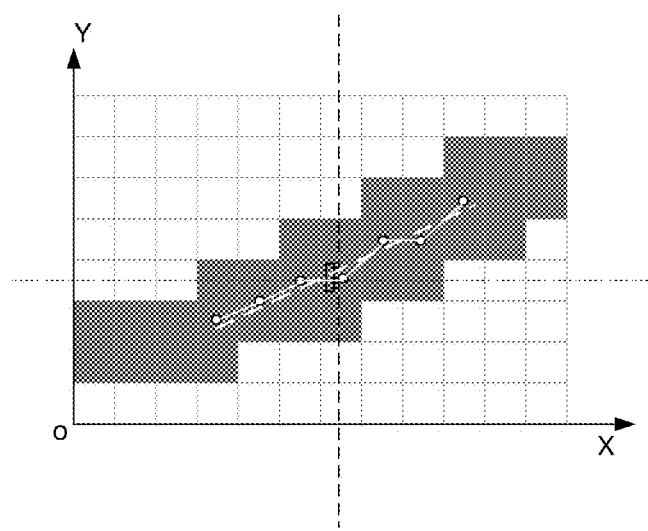
FIG. 3 is a schematic view of calculating the blood vessel direction.

FIG. 3 is a schematic view of calculating blood vessel direction, in which all of the blocks comprise a binary image. The value of the black block is equal to 1, and the white to 0. In this embodiment, the black blocks stand for the flow region and the white blocks stand for background region. Given "★" as the computing point, there are six points in the flow region connected to the computing point in the horizontal direction (including the computing point itself), and three points in the flow region in the vertical direction (including the computing point itself); thus the rough direction of the computing point is the horizontal direction.

3. Accurate computation of blood vessel direction may then be performed, which is based on the rough estimation of blood vessel direction. An accurate computation is applied to the blood vessel direction with spatial relations between points in current flow region and points in the neighborhood. The specific steps will be further described herein. Firstly, the neighborhood of the computing point is determined, wherein the neighborhood takes the computing point as center and includes a plurality of points in the flow region in the rough direction of the computing point. Secondly, the median line of the blood vessel in the neighborhood is determined. To each point in the neighborhood, midpoints of the blood vessel are counted along the direction which is vertical to the rough direction of the blood vessel. The lines connecting these midpoints comprise the median line of the blood vessel in the neighborhood. In the embodiment as shown in FIG. 3, the rough direction of "★" is the horizontal direction. Given the computing neighborhood take the "★" as center and three pixels respectively in the left and right sides. The "○" shown in FIG. 3 is the midpoint of the blood vessel in the neighborhood. The white solid lines lined up by these midpoints are regarded as the median line of the blood vessel in the neighborhood (step 204).

With the median line of the blood vessel, a linear fitting or Hough Transform can be applied to obtain the direction of the blood vessel (step 206). As shown in FIG. 3, the white dotted line is the fitted line. The angle θ between the blood vessel direction of "★" and the horizontal direction can be calculated according to the slope of the straight line.

The binarization of the image is used for convenience. The step, which distinguishes the flow region and the background region, is not necessary at the beginning. The distinguishing step can be used to distinguish the current point is background or flow in other steps.

Figure 4:
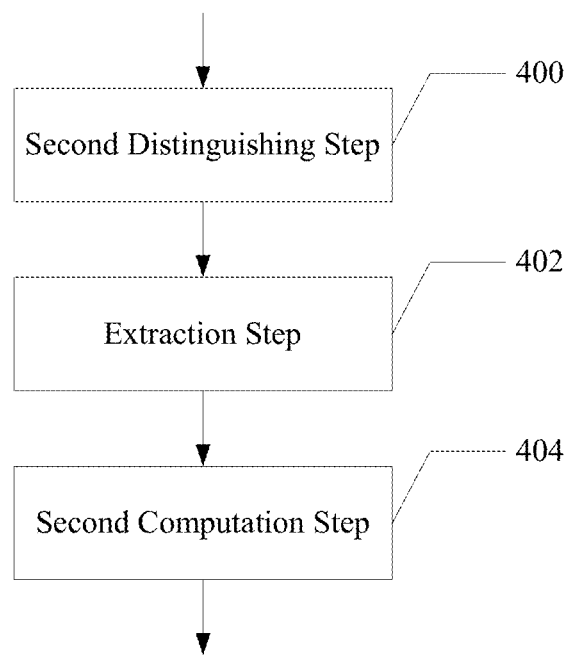
FIG. 4 is a flowchart of a method for calculating the blood vessel direction of the flow velocity image.

In one embodiment, the blood vessel direction is calculated based on morphological characteristics, which comprises a second distinguishing step 400, an extraction step 402, and a second computation step 404, as illustrated in FIG. 4. The blood vessel direction is calculated with the skeleton extracted by morphology, wherein the skeleton is used to express the shape and structure of a flat region with a simplified diagram. The detailed process is as follow:

1. The Image distinguishing (step 400) is performed, which is similar to step 200.

2. Extracting the skeleton of the distinguished image (step 402) is also preformed. Additionally, before extracting the skeleton, a preprocess, such as denoising and edge smoothing, can be applied to the distinguished binarization image so as to deburr the extracted skeleton for achieving a best effect.

3. Calculating the direction of each point on the skeleton may be further performed. The skeleton includes a plurality of lines, so the direction of the point on the skeleton can be calculated by utilizing method of linear fitting or Hough transform to a plurality of neighbor points (step 404).

Additionally, to calculate the point not on the skeleton, as the skeleton is a simplification of a flat region, the direction of the point of the skeleton is regarded as the direction of points not on the skeleton, wherein the point of the skeleton is nearest to the points not on the skeleton and can be lined up in the blood flow region in the distinguished image.

Figure 5:
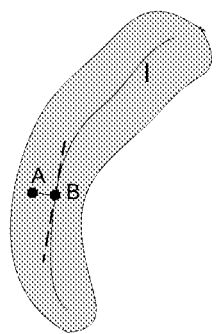
FIG. 5 is a schematic view illustrating a computation method of blood vessel direction based on morphology.

FIG. 5 is a schematic view of computing blood vessel direction based on the skeleton, in which the curve/is the deburred skeleton, point A is the computing point, point B is the nearest point to point A on the skeleton, the dotted line is the direction of point B, thus the direction of point B can be regarded as the direction of point A.

Additionally, the direction of the blood vessel can be calculated with gradient properties, wherein the gradient properties are about the velocity or energy at the center of blood vessel being higher than that at the both sides and degression on both sides in the velocity image or energy image. A skilled artisan will appreciate that the algorithms used in calculating the blood vessel direction include, but are not limit to the described methods herein. Various methods, which are used in dynamic frame persistence by calculating blood vessel direction, may also be used.

In the described embodiments, the blood vessel direction is calculated with the result of the previous frame persistence. It can be understood by those skilled in the art that the flow directions are identical without any change in each of the flow velocity image series or each frame persistence result. Therefore, similarly, the blood vessel direction can be calculated with current frame persistence or other previous frame persistence, and should not be limited in with previous frame persistence.

After determining the blood vessel direction, the result $F_{i-1}$ of previous frame persistence needs to be offset (step 104). The information about blood vessel direction and flow direction is needed when offset. The information about the shape and structure of blood vessel can be identified by the blood vessel direction. However, the direction along which the blood flows cannot be judged. The flow direction can be obtained with Doppler properties; that is, if the flow velocity is positive, the blood flows towards to the transducer, whereas, if the flow velocity is negative, the blood flows away from the transducer.

Figure 6:
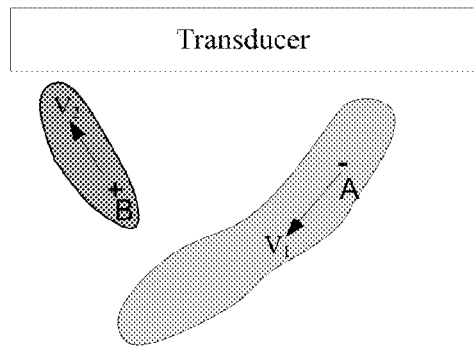
FIG. 6 is a schematic view illustrating judgment of flow movement direction.

With the information about the directions of blood vessel and the flow, the movement direction of flow can be judged. An example is shown in FIG. 6, in which the velocity of point A is negative, which means the blood flows away from the transducer. According to the blood vessel direction, the movement direction of point A is judged as $V_1$. Similarly, the velocity of point B is positive, which means the blood flow toward the transducer. According to the blood vessel direction, the movement direction of point B is judged as $V_2$.

The offset can be obtained by velocity. The larger the velocity, the larger the offset, whereas, the smaller the velocity, the smaller the offset. The relationship between the offset tran and the velocity V can be expressed with a function tran=$f(V)$, where the function f can be set with actual needs. The function f can be linear function or quadratic function, as long as it meets the requirement of the larger the flow, the larger the offset.

For example, the relation between the offset tran and the velocity V can be expressed with a function tran=V×S/(128×fp), where fp is frame rate, S is the Scale set by user, V×S/128 is the flow velocity detected, 1/fp is the interval between two adjacent frames, thus V×S/(128×fp) is the distance of flow between two moments of two frames.

A skilled artisan will appreciate that, by multiplying the flow velocity V with the interval of the two frames, the distance of flow between two moments of two frames is obtained, and the distance is regarded as the offset.

Due to the angle of emission and other reasons, the velocity detected by an ultrasonic instrument under C mode is generally not the real flow velocity. Therefore, the formula can be transformed according to actual situations. For example, the formula can be tran=k×V×S/(128×fp)+b, where k is a constant set with actual needs, the contract between high speed flow and low speed flow can be raised when k>1, while the flow velocity trends to consistent when k<1. To get the effect, the formula can be transformed with double transform, log transform, Gamma transform, etc. However, no matter what transform method, it needs to meet the requirement that the higher the flow velocity, the larger the offset.

Having such described information, the result of the previous frame persistence can be offset. In one embodiment, the detailed process is as follows.

1. Decomposing offset with the blood vessel direction. The offset tran is decomposed in the horizontal and vertical directions, respectively, according to the blood vessel direction. After decomposition, the offset can be expressed as ($\Delta i, \Delta j$) where $\Delta i$=tran cos θ, $\Delta j$=tran sin θ and θ is the angle between the directions of blood vessel and horizon.

Figure 7:
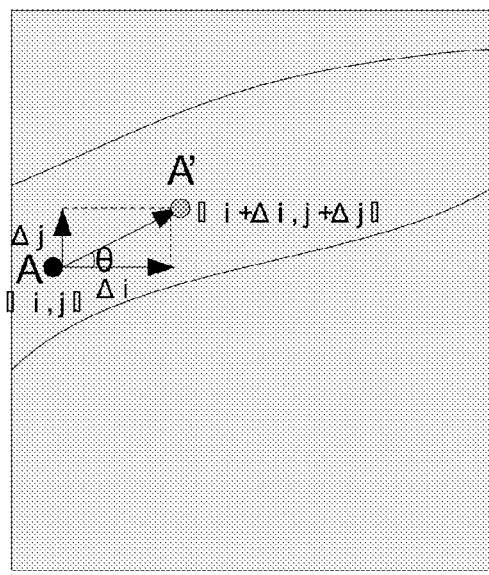
FIG. 7 is a schematic view of flow offset.

2. Offsetting velocity image with the decomposed offsets. After obtaining the horizontal and vertical offsets, the point is offset a distance ($\Delta i, \Delta j$) along the flow direction. FIG. 7 shows an example of an offset, in which the point A is offset ($\Delta i, \Delta j$) along the blood vessel direction according to the flow direction, and the point A' is obtained.

Additionally, as the offsets of each point in the flow region might not be identical, a plurality of points in the flow region might be offset to a same point after offset, which will lead to some points in the flow region have no value after offset. In such case, an interpolation can be utilized (step 106). The method of interpolation can be used according to practical situations.

Figure 8:
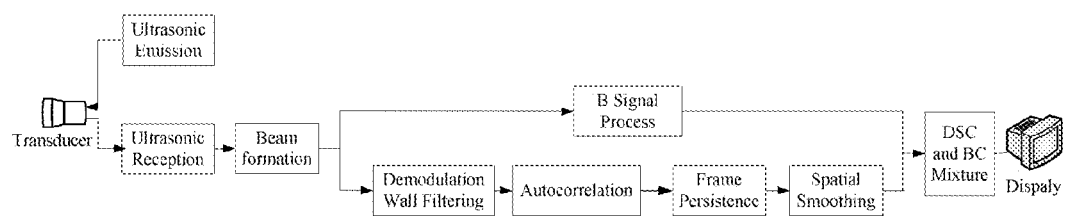
FIG. 8 is a block diagram of a color ultrasonic system.

After offsetting the result of previous frame persistence, the offset result is still marked as $F_{i-1}$, an operation of frame persistence is applied to $F_{i-1}$ and $I_i$ to obtain the result $F_i$=$\phi$($I_i, F_{i-1}$) of current frame persistence (step 108). The result of the current frame persistence is processed by other signal processing techniques shown in FIG. 8, and finally sent to a display. With the frame persistence according to the described embodiment, the flow displayed shows the blood flows along the blood vessel direction, and more satisfies the principle of hemodynamics.

Figure 9:
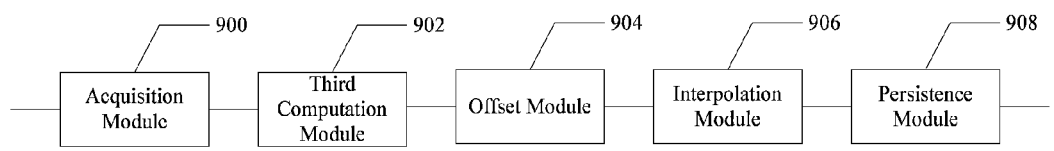
FIG. 9 is a block diagram of a system for color flow dynamic frame persistence.

As illustrated in FIG. 9, a system for color flow dynamic frame persistence may include an acquisition module 900, a third computation module 902, an offset module 904 and a persistence module 908. An interpolation module 906 may also be included in some embodiments. The acquisition module 900 is configured to acquire the result of previous frame persistence of the flow velocity image, as well as the current flow velocity image. The third computation module 902 is configured to calculate the blood vessel direction reflected by the result of the previous frame persistence. The offset module 904 is configured to offset the result of previous frame persistence along the vessel direction with the flow direction and the flow velocity. The interpolation module 906 is configured to interpolate points in the flow region having no value after offset. The persistence module 908 is configured to carry out an operation of frame persistence between the current flow velocity image and the frame persistence result of the previous frame which has been offset. In an embodiment, the third computation module 902 is configure for calculating the blood vessel direction with gradient properties, wherein the gradient properties are about the velocity or energy at the center of blood vessel is higher than that at the both sides and degression on both sides in velocity image or energy image. In another embodiment, the offset module 904 is configured to decompose the offset of the points in the velocity image along vertical and horizontal directions respectively based on the blood vessel direction, and offset the point with a horizontal and vertical offset along the flow direction, implementing the offset of the frame persistence of the previous frame.

Figure 10:
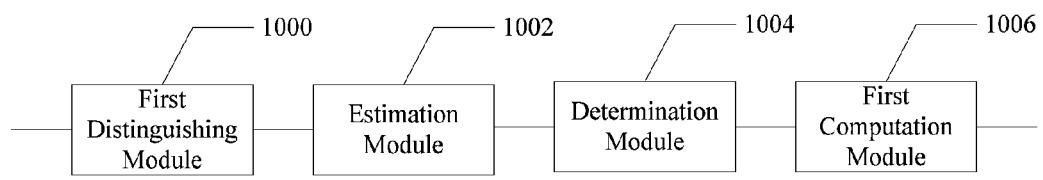
FIG. 10 is a block diagram of a system for calculating blood vessel direction of flow velocity image.

As illustrated in FIG. 10, a system for calculating the blood vessel direction on a flow velocity image comprises a first distinguishing module 1000, an estimation module 1002, a determination module 1004, and a first computation module 1006. The first distinguishing module 1000 is configured to distinguish the points in the flow region and points in the background from a flow velocity image. The estimation module 1002 is configured to set a plurality of directions, respectively calculate the number of the points in the flow region connecting with the computing point in each direction, and take the direction with the maximum number as the rough direction of the computing point. The determination module 1004 is configured to determine midpoints on the direction vertical to the rough direction in a neighborhood, and take the line connecting the midpoints as the median line of the blood vessel in the neighborhood, wherein the neighborhood takes the computing point as the center and consists of a plurality of points in the flow region on the rough direction. The first calculation module 1006 is configured to calculate the direction of the blood vessel on the computing point according to the determined median line of the blood vessel. In one embodiment, the image is binarized by marking the points whose value are smaller than a predefined threshold as zero and the remaining points as 1, thus distinguishing the points in the flow region and the points in the background region.

Figure 11:
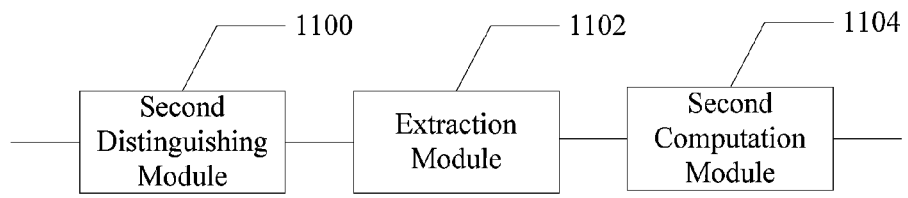
FIG. 11 is a block diagram of a system for calculating blood vessel direction of flow velocity image.

As illustrated in FIG. 11, a system for calculating the blood vessel direction on the flow velocity image comprises a second distinguishing module 1100, an extraction module 1102, and a second computation module 1104. The second distinguishing module 1100 is configured to distinguish each of the points in the flow velocity image into points in the flow region and points in the background region. The extraction module 1102 is configured to extract the skeleton of the flow region from the distinguished image. The second calculation module 1104 is configured to calculate the direction of each point of the skeleton according to a plurality of neighbor points of each computing point of the skeleton, wherein the direction of point of the skeleton is regarded as the direction of points not on the skeleton, and wherein the point of the skeleton is nearest to the points not on the skeleton and can be lined up in the flow region in the distinguished image.

According to the aforesaid embodiments of the disclosure, a system for color flow dynamic frame persistence and a system for calculating blood vessel direction in a flow velocity image can be realized in a color ultrasonic imaging system with hardware, software, firmware or their combination.

While specific embodiments and applications of various methods and devices have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed. Additionally, the terms mentioned in the claims and/or descriptions, such as "first", "second", "third", etc., are used for convenience and should not be construed as limiting.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer or other electronic device. Alternatively, the steps may be performed by hardware components that contain specific logic for performing the steps, or by any combination of hardware, software, and/or firmware.

Embodiments of the present invention may also be provided as a computer program product including a non-transitory machine-readable medium having stored thereon instructions that may be used to program a computer (or other electronic device) to perform processes described herein. The machine-readable medium may include, but is not limited to, floppy diskettes, optical disks, CD-ROMs, DVD-ROMs, ROMs, RAMs, EPROMs, EEPROMs, magnetic or optical cards, or other type of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. An image processing method for calculating blood vessel direction of a flow velocity image comprising a plurality of point-regions, each point-region associated with a central point, the method comprising:
   distinguishing each of the point-regions in the flow velocity image as point-regions in a flow region and point-regions in a background region;
   estimating a rough direction of a computing point-region by:
      setting a plurality of directions and respectively calculating the number of point-regions in the flow region connecting with the computing point-region in each direction; and
      taking the direction with the maximum number of point-regions as the rough direction of the computing point-region;
   determining middle point-regions on the direction perpendicular to the rough direction in a neighborhood;
   determining a line connecting the central points of the middle point-regions as a median line of the blood vessel in the neighborhood, wherein the neighborhood is centered on the computing point-region and includes a plurality of point-regions in the flow region in the rough direction; and
   calculating the direction of the blood vessel on the computing point-region according to the determined median line of the blood vessel,
   wherein calculating comprises applying a linear fitting or Hough Transform to the determined median line of the blood vessel.

2. The method of claim 1, wherein distinguishing comprises binarizing the image by marking the point-regions whose values are smaller than a predefined threshold as zero and the remaining point-regions as one, thereby distinguishing the point-regions in the flow region and the point-regions in the background region.

3. The method of claim 1 wherein the plurality of directions is selected from the group consisting of two directions, or four directions, and eight directions.

4. The method of claim 3, wherein the plurality of directions is selected from the group consisting of a set of directions comprising horizontal and vertical directions, and a set of directions comprising 0°, 45°, 90° and 135°.

5. A system for calculating blood vessel direction of a flow velocity image comprising a plurality of point-regions, each point-region associated with a central point, the system comprising:
   a processor;
   a distinguishing module configured to distinguish each of the point-regions in the blood flow velocity image as point-regions in a flow region and point-regions in a background region;
   an estimation module configured to set a plurality of directions and respectively calculate the number of the point-regions in the flow region connecting with a computing point-region each direction, and take the direction with the maximum number as the rough direction of the computing point-region;
   a determination module configured to determine middle point-regions on the direction perpendicular to the rough direction in a neighborhood;
   determining a line connecting the central points of the middle point-regions as a median line of the blood vessel in the neighborhood, wherein the neighborhood takes the computing point-region as a center point-regions and comprises a plurality of point-regions in the flow region in the rough direction; and
   a computation module configured to calculate the direction of the blood vessel on the computing point-region according to the determined median line of the blood vessel,
   wherein the computation module is configured to applying a linear fitting or Hough Transform to the determined median line of the blood vessel.

6. The system of claim 5, wherein the first distinguishing module is configured to binarize the image by marking the point-regions whose values are smaller than a predefined threshold as zero and the remaining point-regions as 1, thereby distinguishing the point-regions in the flow region and the point-regions in the background region.

7. The system of claim 5, wherein the plurality of directions comprises two directions, or four directions, or eight directions.

8. A non-transitory computer-readable medium comprising program code that causes a processor to perform operations for calculating blood vessel direction of a flow velocity image comprising a plurality of point-regions, each point-region associated with a central point, the operations comprising:
   distinguishing each of the point-regions in the flow velocity image as point-regions in a flow region and point-regions in a background region;
   estimating a rough direction of a computing point-region by setting a plurality of directions and respectively calculating the number of point-regions in the flow region connecting with the computing point-region in each direction, and taking the direction with the maximum number of point-regions as the rough direction of the computing point-region;
   determining middle point-regions on the direction perpendicular to the rough direction in a neighborhood;
   determining a line connecting the central points of the middle point-regions as a median line of the blood vessel in the neighborhood, wherein the neighborhood is centered around the computing point-region and includes a plurality of point-regions in the flow region in the rough direction; and
   calculating the direction of the blood vessel on the computing point-region according to the determined median line of the blood vessel,
   wherein calculating comprises applying a linear fitting or Hough Transform to the determined median line of the blood vessel.

* * * * *